(12) United States Patent
Norman et al.

(10) Patent No.: US 7,754,906 B2
(45) Date of Patent: Jul. 13, 2010

(54) TI, TA, HF, ZR AND RELATED METAL SILICON AMIDES FOR ALD/CVD OF METAL-SILICON NITRIDES, OXIDES OR OXYNITRIDES

(75) Inventors: John Anthony Thomas Norman, Encinitas, CA (US); Xinjian Lei, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 617 days.

(21) Appl. No.: 11/522,768

(22) Filed: Sep. 18, 2006

(65) Prior Publication Data

US 2007/0082500 A1    Apr. 12, 2007

Related U.S. Application Data

(60) Provisional application No. 60/724,757, filed on Oct. 7, 2005.

(51) Int. Cl.
    C07F 7/18    (2006.01)
(52) U.S. Cl. .......................................... 556/9
(58) Field of Classification Search ............... 556/9
    See application file for complete search history.

(56) References Cited

U.S. PATENT DOCUMENTS

| | | | |
|---|---|---|---|
| 5,603,988 | A | 2/1997 | Shapiro et al. |
| 6,403,465 | B1 | 6/2002 | Liu et al. |
| 6,426,117 | B1 | 7/2002 | Yi et al. |
| 6,559,074 | B1 | 5/2003 | Chen et al. |
| 7,232,464 | B2 | 6/2007 | Mathieu et al. |
| 2002/0127883 | A1 | 9/2002 | Conti et al. |
| 2003/0190423 | A1 | 10/2003 | Yang et al. |
| 2003/0190804 | A1 | 10/2003 | Glenn et al. |
| 2004/0009336 | A1 | 1/2004 | Marcadal et al. |
| 2004/0197492 | A1 | 10/2004 | Chen et al. |

FOREIGN PATENT DOCUMENTS

| | | |
|---|---|---|
| CN | 1620271 A | 5/2005 |
| JP | 09-104984 A | 4/1997 |
| JP | 2001-230248 | 8/2001 |
| WO | 03/070128 A1 | 8/2003 |

OTHER PUBLICATIONS

Brauer et al., Journal of Organometallic Chemistry, 1980, pp. 343-351.*

XP-002414874; Passarelli, Vincenzo, et al; "Unsymmetrically Substituted Dimethyldiaminosilanes as Ligands towards Zirconium (IV)"; European Journal of Inorganic Chemistry; 2004; pp. 4439-4446.

XP-002414875; Kim, Sung-Joon, et al; "Titanium Complexes Incorporating 1,1-Bis(tert-butylamido)-1-Silacycloalkane Ligands: Generation of Alkyl Derivatives and Reactivity Toward Molecular Oxygen"; Organometallics; 2004, pp. 559-567.

XP-002414876; Kim,Sung-Joon, et al; "Sterically Controlled Silacydoalkyl Diamide Complexes f Titanium (IV): Synthesis, Structure, and Catalytic Behavior of (cycl)Si(NBut)2TiCl2 [(cycl)] Si=Silacyclobutane, Silacyclopentane, Silacyclopentene, and Silacyclohexane"; Organometallics; 2001; pp. 2136-2144.

XP-002414877; Brauer, D.J., et al; "Cyclic Silylamides of Vanadium, Niobium, Tantalum and Hafnium. Crystal and Molecular Structures of Spirocyclic Tetraamides of Vanadium(IV), Methylniobium(V), and Hafnium(IV)"; Journal of Organometallic Chemistry; 1986; pp. 317-332.

XP-002414878; Brauer, D.J., et al; "Titan-Stickstoff-Verbindungen XXIX. Kristall-und Molekulstruktur Spriocyclischer Amide von Titan und Zirconium mit dem Liganden Me2Si(N-tert-Bu)2"; Journal of Organometallic Chemistry; 1980; pp. 343-351 (English Abstract).

Passarelli, et al; "Unsymmetrically Substituted Dimethyidiaminosilanes as Ligands Towards Zirconium (IV)"; Eur. J. Inorg. Chem.; 2004; pp. 4439-4446.

Gibson, et al; "High Activity Ethylene Polymerisation Catalysts Based on Chelating Diamide Ligands"; Chem. Commun.; 1998; pp. 313-314.

Alen, P., T. Aaltonen, M. Ritala, M. Leskela, T. Sajavaara, J. Keinonen, J.C. Hooker, and J.W. Maes. ALD of Ta(Si)N Thin Films Using TDMAS as a Reducing Agent and as a Si Precursor. *Journal of the Electrochemical Society*. 2004. 151(8). G523-G527.

Brauer, D.J., H. Buerger, E. Essig and W. Gescheandtner. Titanium-Nitrogen Compound. XXIX. Crystal and Molecular Structure of Spriocyclic Amides of Titanium and Zirconium wit the Ligand Me2Si(N-tert-BU)2. *Journal of Organometallic Chemistry*. 1980. 190. 343-351.

Buerger, H. and D. Beiersdorf. Cyclic titanium amides with silatitanadiazacyclobutane structure. *Zeitschrift fuer Anorganische und Allgemeine Chemie*. 1979. 459. 111-18.

(Continued)

Primary Examiner—Joseph R Kosack
(74) Attorney, Agent, or Firm—Lina Yang

(57) ABSTRACT

An organometallic complex represented by the structure:

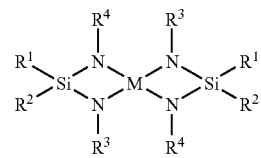

wherein M is a metal selected from Group 4 of the Periodic Table of the Elements and $R^{1-4}$ can be same or different selected from the group consisting of dialkylamide, difluoralkylamide, hydrogen, alkyl, alkoxy, fluoroalkyl and alkoxy, cycloaliphatic, and aryl with the additional provision that when $R^1$ and $R^2$ are dialkylamide, difluoralkylamide, alkoxy, fluoroalkyl and alkoxy, they can be connected to form a ring. Related compounds are also disclosed. CVD and ALD deposition processes using the complexes are also included.

3 Claims, 4 Drawing Sheets

OTHER PUBLICATIONS

Grocholl, L. V., Huch, L. Stahl, R.J. Staples, P. Steinhart, and A. Johnson. Monomeric, Four-Coordinate Group 4 Metal Complexes with Chelating Bis(tert-butylamido) cyclodisilazane Ligands: Syntheses and Molecular Structures of $((MeSiNBu)_2(NBu)_2)MMe_2$, M = Zr, Hf. *Inorganic Chemistry*. 1997. 36. 4451-4457.

Kim, S.-J., D.-W. Choi, Y.-J. Lee, B.-H. Chae, J. Ko and S.O. Kang. Titanium Complexes Incorporating 1, 1- Bis(tert-butylamido)-1-silacycloalkane Ligands: Generaton of Alkyl Derivatives and Reactivity toward Molecular Oxygen. *Organometallics*. 2004. 23. 559-567.

Kim, S.J., I.N. Jung, B.R. Yoo, S.H. Kim, J. Ko, D. Byun and S.O. Kang. Sterically Controlled Silacycloalkyl Diamide Complexes of Titanium (IV): Synthesis, Structure, and Catalytic Behavior of $(cycl)Si(NBU)_2TiCl_2$ [(cycl)Si = Silacyclobutane, Silacyclopentane, Silacyclopentene, and Silacyclohexane]. *Organometallics*. 2001. 20. 2136-2144.

Marcadal, C., M. Eizenberg, A. Yoon, and L. Chen. Metallorganic Chemical Vapor Deposited TiN Barrier Enhancement with $SiH_4$ Treatment. *Journal of the Electrochemical Society*. 2002. 149. C52-C58.

Min, J.-S., J.-S. Park, H.-S. Park, and S.-W. Kang. The Mechanism of Si Incorporation and the Digital Control of Si Content during the Metallorganic Atomic Layer Deposition of Ti-Si-N. Thin Films. *Journal of Electrochemical Society*. 2000. 147. 3868-3872.

Xiaozhan Liu, Z.W., Hu Cai, Yihui Yang, Tianniu Chen, Catherine E. Vallet, Ray A. Zuhr, David B. Beach, Zhi-Hui Peng, Yun-Dong Wu, Thomas E. Conolino, Arnold L. Rheingold, and Ziling Xue. Reactions of Tetrakis(dimethylamide)—Titanium, —Zirconium and —Hafnium with Silanes: Synthesis of Unusual Amide Hydride Complexes and Mechanistic Studies of Titanium-Silicon-Nitride (Ti-Si-N) Formation. *Journal of the American Chemical Society*. 2001. 123. 8011-8021.

Passavelli, V., et al; "Unsymmectrically Substituted Dimethyldiaminosilanes as Ligands Towards Zirconium (IV)"; Eur. J. Inorg. Chem.; 2004; pp. 4439-4446.

Bauer, D.J., et al; "XXIX.* Crystal and Molecular Structure of Spirocyclic Amides of Titanium and Zirconium with the Ligands Me2Si(N-t-Bu)2"; Journal of Organometallic Chemistry; vol. 190; pp. 343-351; 1960.

Brauer, D.J., et al; "Cyclic Silylamides of Vanadium, Niobium, Tantalum and Hafnium, Crystal and Molecular Structures of Spirocylic Tetraamides of Viv, Ch3Nbv and Hfiv"; Journal of Organometallic Chemistry; vol. 310; pp. 317-332; 1986.

Passarelli, V., et al; "Unsymmectrically Substituted Dimethyldiaminosilanes as Ligands Towards Zirconium(IV)"; European Journal of Inorganic Chemistry; vol. 22; pp. 4439-4446; 2004.

Passarelli, V, et al; "Synthesis and Characterisation of Novel Zirconium(IV) Derivatives Containing the Bis-Amido Ligand SiMe2(NRR)2"; Vol. Dalton Transacations; vol. 7; pp. 1411-1418; 2003.

Kim, S., et al; "Sterically Controlled Silacycloalkyl Diamide Complexes of Titanium(IV): Synthesis, Structure, and Catalytic Behavior of (cycl)Si(NBuf)2TiCl2 [(cycl)Si= Silacyclobutane, Silacyclopentane, Silacyclopentene, and Silacyclohexane]"; Organometallics, vol. 20, No. 11; pp. 2136-2144; 2001.

Kim, S., et al; "Titanium Complexes Incorporating 1,1-Bis(tert-butylamido)-1-silacycloalkane Ligands: Generation of Alkyl Derivatives and Reactivity Toward Molecular Oxygen"; Organometallics, vol. 23, No. 3; pp. 559-567; 2004.

* cited by examiner

TI, TA, HF, ZR AND RELATED METAL SILICON AMIDES FOR ALD/CVD OF METAL-SILICON NITRIDES, OXIDES OR OXYNITRIDES

CROSS-REFERENCE TO RELATED APPLICATIONS

This application claims benefit of U.S. Provisional Application No. 60/724,757, filed Oct. 7, 2005. The disclosure of this provisional application is hereby incorporated by reference.

BACKGROUND OF THE INVENTION

The field of the present invention is copper diffusion barrier layers in the fabrication of integrated circuits to avoid the migration of copper or other metals deposited as metal lines into insulating layers and other layers, features and semiconductor materials during the deposition and subsequent treatment of the metal line fabrication. The invention is also related to thin films as electrodes or dielectric layers in the semi-conductor industry.

BRIEF SUMMARY OF THE INVENTION

The present invention is an organometallic complex represented by the structure:

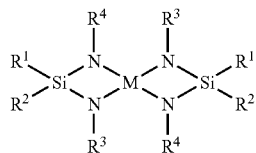

wherein M is a metal selected from Group 4 of the Periodic Table of the Elements and $R^{1-4}$ can be same or different selected from the group consisting of dialkylamide, difluoralkylamide, hydrogen, alkyl, alkoxy, fluoroalkyl and alkoxy, fluoroalkoxy, cycloaliphatic, and aryl with the additional provision that when $R^1$ and $R^2$ are dialkylamide, difluoralkylamide, alkoxy, fluoroalkyl or alkoxy or fluoroalkoxy, they can be connected to form a ring.

In a preferred embodiment, the present invention is bis(N,N'-di(tert-butyl)-diaminosilyl)titanium as represented below.

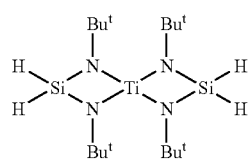

An organometallic complex represented by the structure:

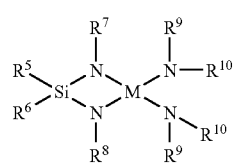

wherein M is a metal selected from Group 4 of the Periodic Table of the Elements and $R^{5-10}$ can be same or different selected from the group consisting of hydrogen, alkyl, alkoxy, fluoroalkyl and alkoxy, fuoroalkoxy cycloaliphatic, and aryl with the additional provision that when $R^5$, $R^6$, $R^9$ and $R^{10}$ are dialkylamide, difluoralkylamide, alkoxy, fluoroalkyl alkoxy or fluoroalkoxy, they can be connected to form a ring.

An organometallic complex represented by the structure:

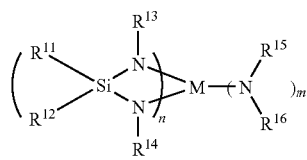

wherein M is a metal selected from Group 5 of the Periodic Table of the Elements and $R^{11-16}$ can be same or different selected from the group consisting of, hydrogen, alkyl, alkoxy, fluoroalkyl and alkoxy, fluoroalkoxy, cycloaliphatic, and aryl; n=1,2, m=5−2n, wherein when $R^{11}$, $R^{12}$, $R^{15}$ and $R^{16}$ are dialkylamide, difluoralkylamide, alkoxy, fluoroalkoxy, fluoroalkyl or alkoxy, they can be connected to form a ring.

An organometallic complex represented by the structure:

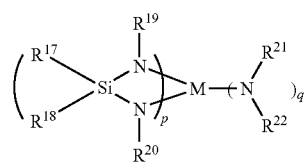

wherein M is a metal selected from Group 6 of the Periodic Table of the Elements and $R^{17-22}$ can be same or different selected from the group consisting of, hydrogen, alkyl, alkoxy, fluoroalkyl and alkoxy, cycloaliphatic, and aryl; p=1, 2,3, q=6−2p, wherein when $R^{17}$, $R^{18}$, $R^{21}$ and $R^{22}$ are dialkylamide, difluoralkylamide, alkoxy, floroalkoxy, fluoroalkyl or alkoxy, they can be connected to form a ring.

Chemical vapor deposition (CVD) and atomic layer deposition (ALD) processes using these complexes are also contemplated.

DETAILED DESCRIPTION OF THE INVENTION

Figure 1:
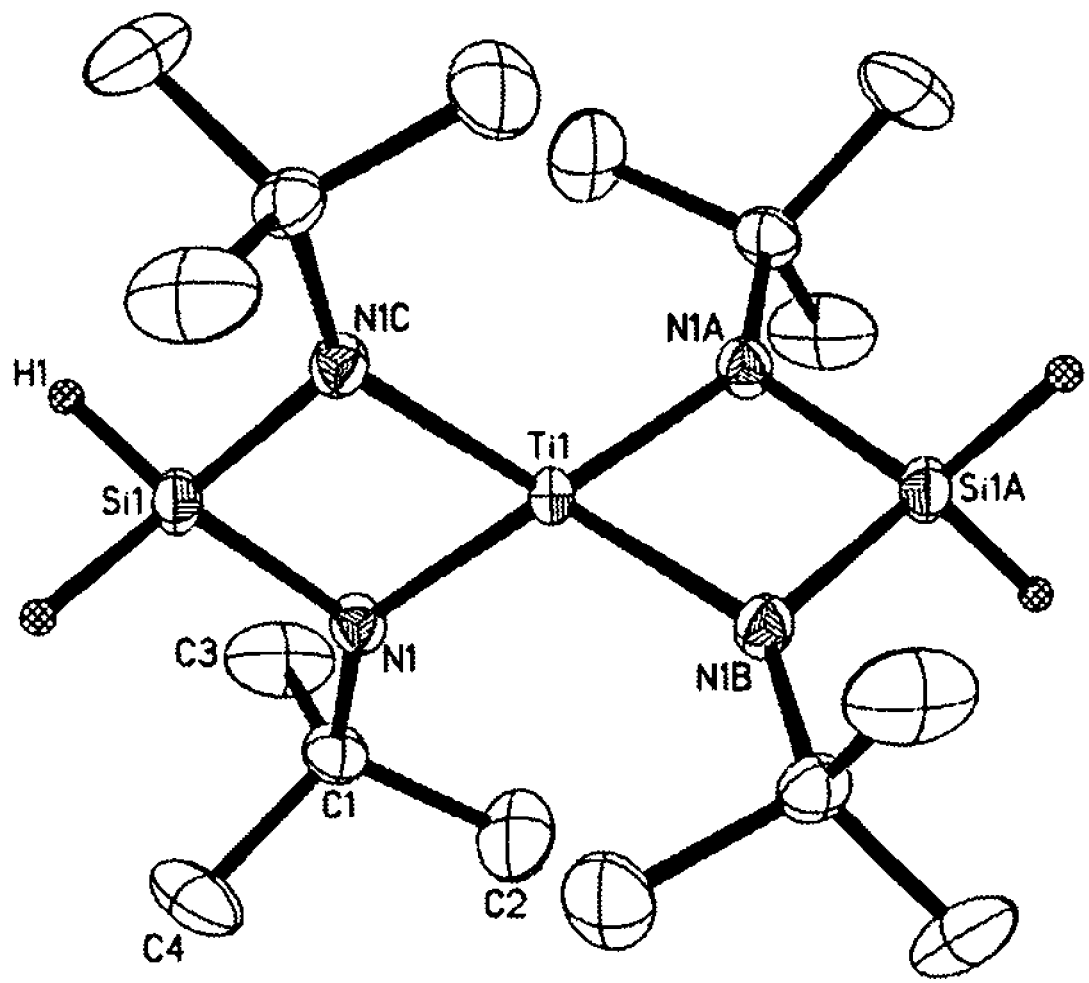
FIG. 1 is a single crystal structure of of bis(N,N'-di(tert-butyl)diaminosilyl)titanium for use in the CVD or ALD of titanium silicon nitride containing films.

Copper has now effectively replaced aluminum as the interconnect metal for semiconductor logic devices due to it superior electrical conductivity and high electromigration resistance. However, copper can quickly and destructively diffuse through other materials in the device such as silicon or inter-level dielectrics leading to electrical malfunctioning in the finished product. For these reasons it is necessary to encapsulate the copper with diffusion barriers. Metal nitride and metal silicon nitride thin films are candidate materials for these diffusion barriers. They can also be used close to the silicon surface of a transistor as gate electrode materials, where they pose no contamination threat to the silicon and can be processed at relatively high temperatures. Metal nitride layers, e.g., titanium nitride (TiN) layers have been employed as barrier layers against diffusion, including copper diffusion, in semiconductor device structures, e.g., contacts, vias and trenches. However, these barrier layers must be extremely thin to accommodate the higher aspect ratios of today's devices, since it is desirable for the barrier to contribute the least additional resistance to a copper interconnect as possible. These barriers must be chemically inert and must resist inter-diffusion of adjacent materials through it, have low electrical resistivity (exhibit high conductivity), low contact or via resistance and low junction leakage.

Metal nitrides tend to be metallic compounds than can possess a crystalline structure, whereas the metal nitride/silicon nitride films tend to be amorphous. In the former case, the crystallinity of the film can provide for a breakdown of its barrier properties, since copper diffusion can occur along its crystal grain boundaries. In the latter case, since the materials are amorphous, there are no grain boundaries so barrier properties are improved. From an alternative perspective, the silicon nitride component acts to block the grain boundaries in the metal nitride.

However, as more silicon nitride is added into the metal nitride to achieve this amorphous nature, the electrical resistivity of the material increases so the level of silicon nitride needs to be carefully controlled. Typically these barrier films need to be grown as highly conformal thin films capable of evenly coating deeply etched features on a silicon wafer with a precisely controlled film thickness. These features are ultimately filled with copper to provide the interconnecting electrical pathways between transistor devices at the silicon wafer surface. Chemical vapor deposition ("CVD") is often used to grow these films conformal thin films, but as device dimensions continue to shrink barrier film thicknesses on the order of 10 Angstoms are needed. At this point CVD becomes challenged and atomic layer deposition ("ALD") becomes more attractive. In either case, volatile metal compounds are required as precursors. For metal nitride films, such as titanium nitride, tantalum nitride or tungsten nitride, metal amide or amide/imide compounds are used. These compounds are reacted in an ALD or CVD process with a suitable regent, such as ammonia, to deposit a metal nitride. An example would be the CVD process, which uses the precursor tetrakis (diethylamido)titanium reacting with ammonia to give TiN. Alternatively, a precursor can be thermolysed on the wafer surface in a CVD process to give a continuous thin film of a titanium carbonitride material, which is subsequently annealed using a hydrogen/nitrogen plasma to densify the film and reduce the level of carbon to give a mostly titanium nitride film.

An example of a suitable precursor for the latter process is tetrakis(dimethylamido)titanium. Alternatively, a tantalum nitride film can be grown in an ALD process using the precursor pentakis(dimethylamido)tantalum reacting with ammonia. Alternatively, a tungsten nitride film can be grown by ALD using the precursor (Bu$^t$N=)$_2$W(NMe$_2$)$_2$ reacting in alternating cycles with ammonia. If silicon nitride is to be introduced into these films, it is usually done by co-reacting the metal nitride precursor with a silicon nitride precursor, such as silane or a silicon amide compound, such as tetrakis (dimethylamido)silicon. Thus, a metal (M) containing precursor, a silicon containing precursor and a nitrogen source, such as ammonia, are co-reacted together to give the MSiN film. Thus, the degree of silicon incorporation will depend to some degree upon the ability to precisely control the metering of the silicon precursor during the process.

Currently in the formation of ternary films, a metal amide, silane, and ammonia are sequentially deposited on the substrate via cyclic deposition, but the process poses processing issues. Silane is a pyrophoric gas and creates a potential safety hazard. In addition, three precursors are employed in the cyclic process, requiring three deposition steps along with respective purge steps. On the other hand, aminosilane or hydrazinosilane and ammonia have been reported to form silicon nitride. Importantly, though, it has been found that in these films, there is no direct metal-silicon bond in the metal silicon nitride formed by either chemical vapor deposition or atomic layer deposition, implying metal nitride and silicon nitride are in separate phases in the resulting film, i.e., metal nitride is stuffed with silicon nitride. The present invention is a potentially more elegant approach to growing MSiN films which uses a precursor that already has both the metal and silicon in its structure so both elements are delivered in the same molecule at a precisely fixed ratio, although the exact ratio of metal to silicon in a film resulting from the processing of such a precursor can still be controlled as a function of the exact process conditions of pressure, temperature, energy input and flows. The present invention will be illustrated in several non-limiting examples, set forth below.

EX. 1

Synthesis of bis(N,N'-di(tert-butyl)diaminosilyl) titanium, Ti(H$_2$Si(NBu$^t$)$_2$)$_2$ Under an atmosphere of dry nitrogen, 7.0 g (40 mmoles) of bis(tert-butlyamino)silane were dissolved in 100 ml of dry tetrahydrofuran solvent and cooled to −78° C. To this solution 32.0 ml (840 mmoles) of 2.5 M n-butyl lithium in hexanes were added dropwise over a 10 minute period and the resulting mixture stirred for an additional 30 minutes at −78° C. resulting in the formation of a white precipitate. This mixture was then allowed to warm to room temperature for an additional 20 minutes after which it was re-cooled to −78° C. To a separate vessel containing 10 ml of dry tetrahydrofuran under a nitrogen atmosphere was slowly added 2.14 ml (10 mmoles) of titanium tetrachloride resulting in the formation of a yellow precipitate. This latter precipitate was then added to the first precipitate at −78° C. and then allowed to warm to room temperature and stir overnight. The terahydrofuran and hexane solvents were then stripped of under vacuum and the resulting yellow-green solid was mixed with 100 ml of fresh dry hexane under nitrogen, the resulting mixture filtered and the resulting green oil was heated to 110° C. under dynamic vaccum and distilled over as an orange colored solid into a collection vessel cooled with liquid nitrogen. Yield=3.6. g (45%) This crude product was then further purified by sublimation at 65-70° C. The structure was confirmed by single crystal X-ray analysis (see the drawing in FIG. 1).

$^1$H NMR: (500 MHz, C$_6$D$_6$): δ=1.35 (s, 36H), δ=5.41 (s, 4H). $^{13}$C NMR: (500 MHz, C$_6$D$_6$): δ=35.25 (s, 12C), δ=58.97 (s, 4C).

Mass spectra shows a strong peak at 387 m/z (ie parent of 393 m/z minus CH$_3$ of 15 m/z).

An alternative synthesis may also be used where two equivalents of the dianion of bis(tert-butlyamino)silane are added to titanium tetrachloride in hexanes or dry tetrahydrofuran at −78° C. and the resulting mixture processed as above.

Figure 2:
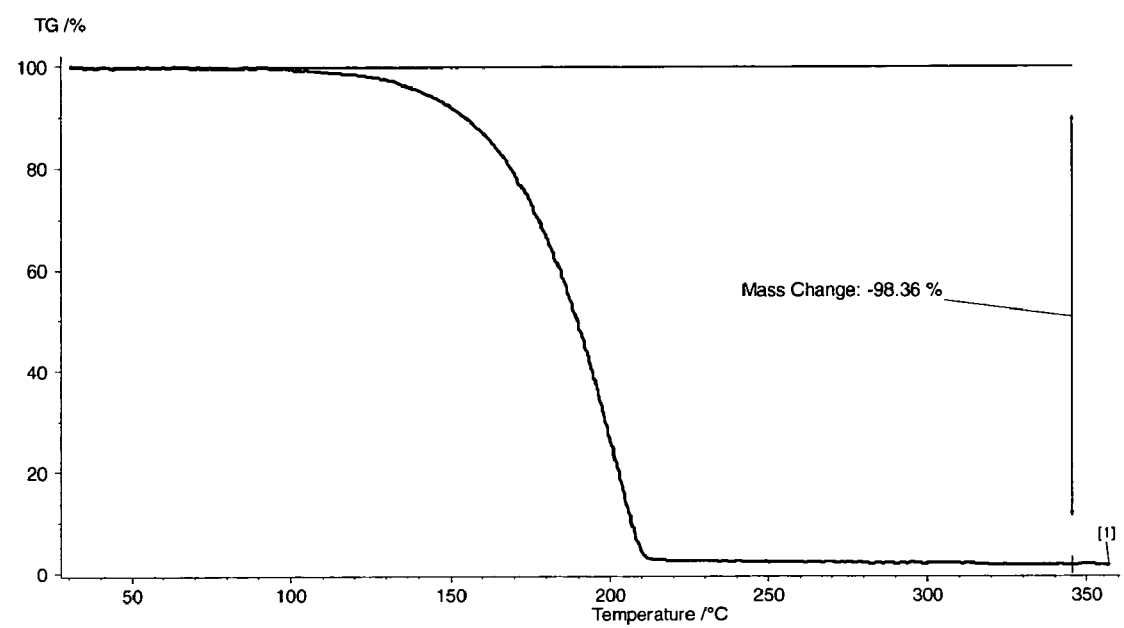
FIG. 2 is a graph of thermal gravimetric analysis (TGA) of bis(N,N'-di(tert-butyl)diaminosilyl)titanium. The almost complete weight loss indicates it is volatile and can be readily delivered into a reaction chamber in a typical CVD or ALD process. Thus, it is a suitable precursor to prepare titanium silicon nitride containing films with and without ammonia or other suitable nitrogen containing reagent.

A graph of thermal gravimetric analysis (TGA) of bis(N,N'-di(tert-butyl)diaminosilyl)titanium was shown in FIG. 2. The almost complete weight loss indicated it was volatile and could be readily delivered into a reaction chamber in a typical CVD or ALD process. Thus, it is a suitable precursor to prepare titanium silicon nitride containing films with and with no ammonia or other suitable nitrogen containing reagent.

EX. 2

Synthesis of HSi(NMe$_2$)(Bu$^t$N)$_2$Ti(NMe$_2$)$_2$

Under an atmosphere of dry nitrogen, 3.48 g (20 mmoles) of bis(tert-butylamino)silane were dissolved in 100 ml of dry tetrahydrofuran solvent and cooled to −78° C. To this solution 24.4 ml (40 mmoles) of 1.6 M n-butyl lithium in hexanes were added dropwise over a 10 minute period and the resulting mixture stirred for an additional 30 minutes at −78° C. resulting in the formation of a white precipitate. This mixture was then allowed to warm to room temperature for an additional 20 minutes after which it was re-cooled to −78° C. To a separate vessel containing 10 ml of dry tetrahydrofuran under a nitrogen atmosphere was slowly added 0.55 ml (5 mmoles) of titanium tetrachloride resulting in the formation of a yellow precipitate. This titanium precipitate was then added to the lithiated mixture at −78° C. To this mixture, 20 g (20 mmoles) of 5 wt % lithium dimethylamide was added maintaining −78. The resulting mixture was then allowed to warm to room temperature and stirred overnight. The solvents were then stripped and the resulting crude product was mixed with 100 ml of dry hexane under nitrogen, filtered and the hexane then removed under vacuum. The resulting oil was then heated to 110° C. under dynamic vaccum and distilled over as an orange colored solid into a collection vessel cooled with liquid nitrogen. This orange colored product was then purified by vacuum sublimation at 60° C.

EX. 3

Formation of Ti—Si—N Films by CVD using Ti(H$_2$Si(NBu$^t$)$_2$)$_2$ as an Organometallic Precursor Ti(H$_2$Si(NBu$^t$)$_2$)$_2$ was used as the organometallic precursor for the formation of metal silicon nitride films in a conventional CVD apparatus using known CVD techniques.

Ti(H$_2$Si(NBu$^t$)$_2$)$_2$ was vaporized in a bubbler at 90° C. and transported into a CVD chamber in combination with and without NH$_3$ as a nitrogen-containing source. The CVD chamber was a cold-wall system having a heated substrate holder. The substrate was maintained at the temperature range from 400 to 500° C. The chamber pressure was maintained at 1 to 2 Torr.

Figure 3:
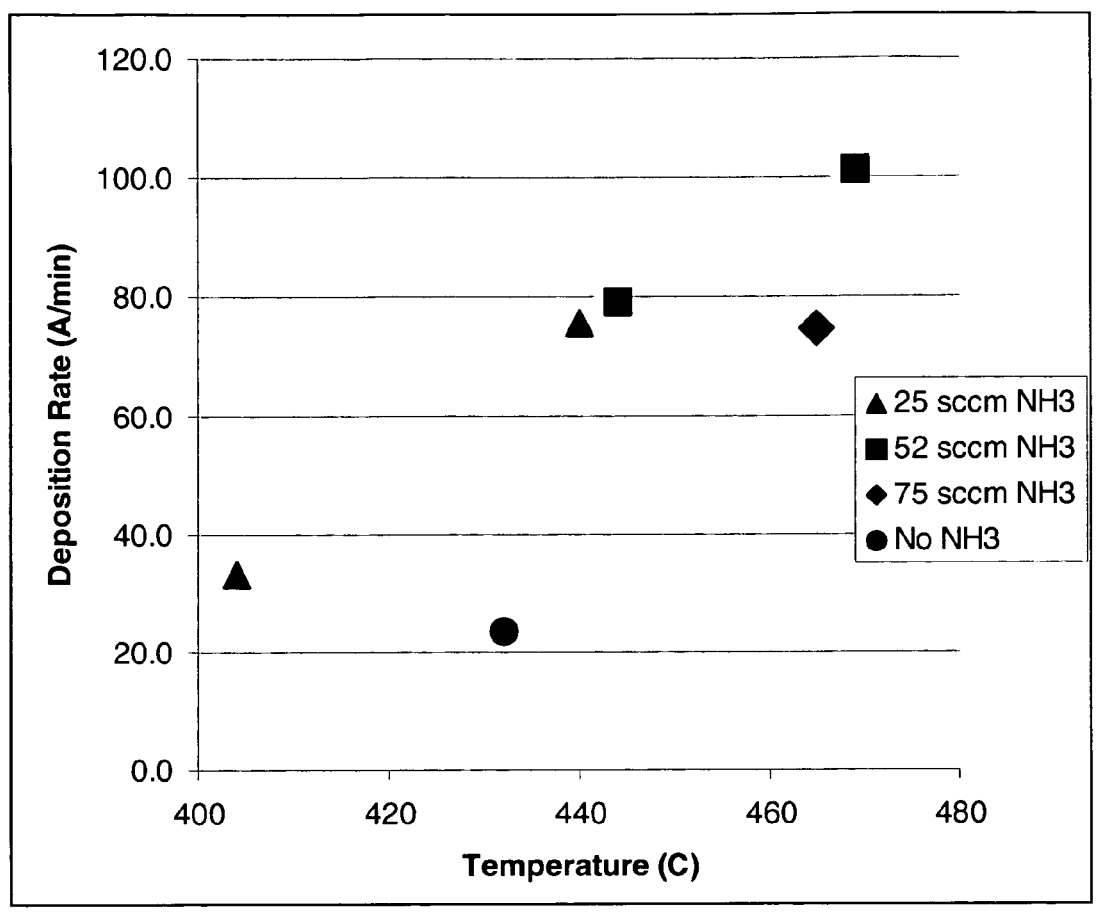
FIG. 3 shows the deposition rate (Å/min) of Ti—Si—N films as a function of substrate temperature at a deposition pressure of 1.5 Torr with a He carrier gas flow rate of 46 sccm with and without ammonia.

The deposition rate of Ti—Si—N films as a function of substrate temperature at a deposition pressure of 1.5 Torr with a He carrier gas flow rate of 46 sccm was shown in FIG. 3. The flow rate of NH$_3$ ranged from 0 sccm (no NH$_3$) to 75 sccm. The deposition rates increased as the substrate temperature increased. The deposition with no NH$_3$ had the lowest deposition rate, indicating the presence of NH$_3$ promoted the formation of titanium siliconitrde films.

Figure 4:
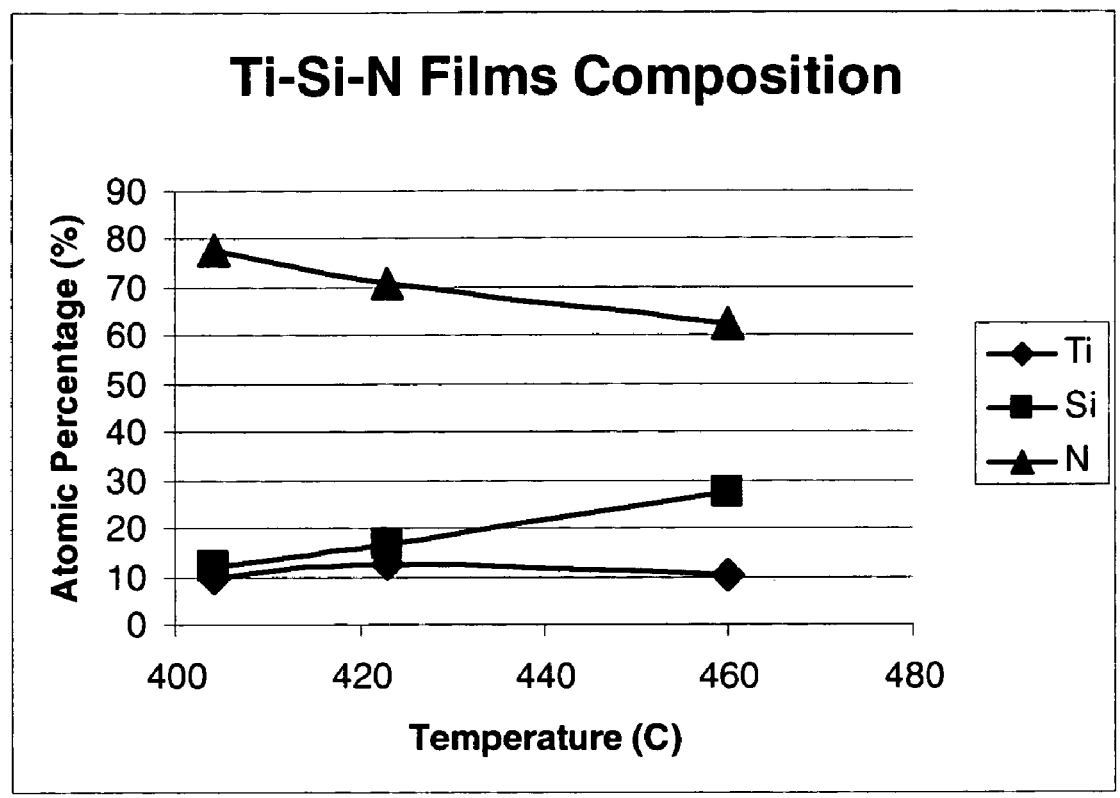
FIG. 4 shows the composition of titanium silicon nitride films at various temperatures. The titanium silicon nitride films are formed from chemical vapor deposition using Ti(H$_2$Si(NBu$^t$)$_2$)$_2$ as organometallic precursor.

EDX analysis of titanium siliconitrde films deposited at various temperatures with NH$_3$ as a nitrogen-containing source indicated that the films contained titanium, silicon, and nitrogen atoms (as shown in FIG. 4).

The invention claimed is:

1. An organometallic complex represented by the structure:

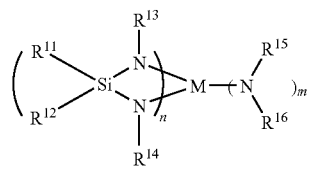

wherein
M is a metal selected from Group 4 of the Periodic Table of the Elements, n=2, m=0, R$^1$ is hydrogen, and R$^{2-4}$ can be same or different selected from the group consisting of dialkylamide, difluoralkylamide, hydrogen, alkyl, alkoxy, fluoroalkoxy, fluoroalkyl, cycloaliphatic, and aryl.

2. The organometallic complex of claim 1 wherein M is a selected from the group consisting of titanium, zirconium and hafnium.

3. The organometallic complex of claim 1 is bis(N,N'-di(tert-butyl)-diaminosilyl)titanium.

* * * * *

UNITED STATES PATENT AND TRADEMARK OFFICE
CERTIFICATE OF CORRECTION

PATENT NO. : 7,754,906 B2 Page 1 of 1
APPLICATION NO. : 11/522768
DATED : July 13, 2010
INVENTOR(S) : John Anthony Thomas Norman and Xinjian Lei It is certified that error appears in the above-identified patent and that said Letters Patent is hereby corrected as shown below:

Column 6, Line 32

In claim 1 delete " 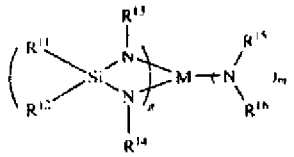 " and insert -- 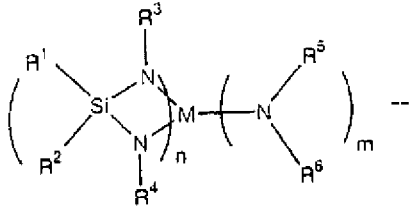 --

Signed and Sealed this

Twelfth Day of October, 2010

David J. Kappos
*Director of the United States Patent and Trademark Office*